United States Patent [19]
Yanik

[11] Patent Number: 5,822,067
[45] Date of Patent: Oct. 13, 1998

[54] OPTICAL ACTIVITY DETECTOR FOR USE WITH OPTICALLY ACTIVE COMPOUNDS

[76] Inventor: Gary W. Yanik, 7289 Garden Rd. #105, Riviera Beach, Fla. 33404

[21] Appl. No.: 962,017

[22] Filed: Oct. 31, 1997

Related U.S. Application Data

[63] Continuation of Ser. No. 594,529, Jan. 31, 1996, abandoned.

[51] Int. Cl.$^6$ .................................................. G01N 21/21
[52] U.S. Cl. ............................................................ 356/368
[58] Field of Search ..................... 356/364, 365, 356/366, 367, 368

[56] References Cited

U.S. PATENT DOCUMENTS

| | | | |
|---|---|---|---|
| 2,753,479 | 7/1956 | Aughey et al. ......................... | 356/313 |
| 3,510,226 | 5/1970 | Cary ....................................... | 356/364 |
| 4,019,372 | 4/1977 | Parkell et al. ......................... | 356/410 |
| 5,408,322 | 4/1995 | Hsu et al. ............................... | 356/369 |

Primary Examiner—Richard A. Rosenberger
Attorney, Agent, or Firm—McHale & Slavin PA

[57] ABSTRACT

An improved optical rotation detector for detecting optically active molecular compounds in a sample solution using: a laser diode with the beam passing through an optical fiber or lens to improve its quality, a reference oscillator at frequency f, a first polarizer, a specially constructed flow cell to minimize mechanical birefringence and leaking in the cell's optical windows, a second polarizer, and an improved detection scheme. The detection scheme includes a first and second photodetector for sensing first and second signals, where the first signal is light passed through the second polarizer and the second signal is light reflected off the second polarizer. A compensator circuit low pass filters the signals, inverts one signal and sums it with the other, and then notch filters off the undesired components to produce a compensated signal. The compensated signal then drives a lock-in amplifier which is driven by the reference oscillator to sense the amplitude modulated f frequency signal. This compensated signal indicates the optical activity of the sample, yet is immune to laser power fluctuations.

16 Claims, 12 Drawing Sheets

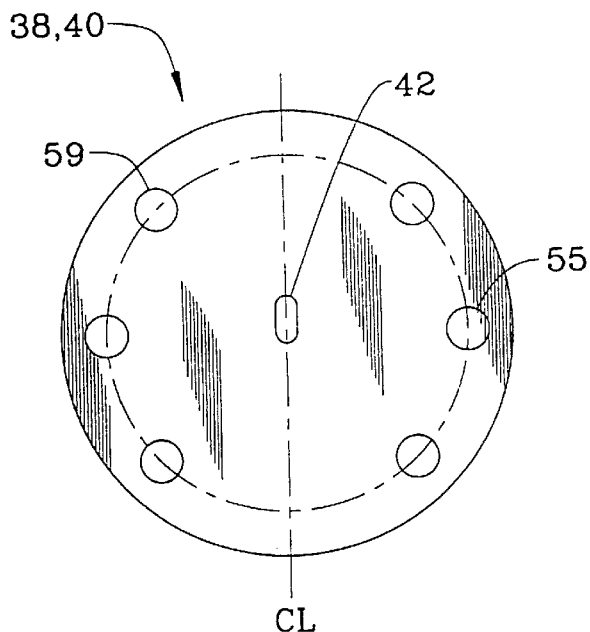
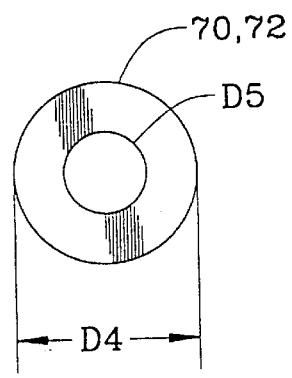
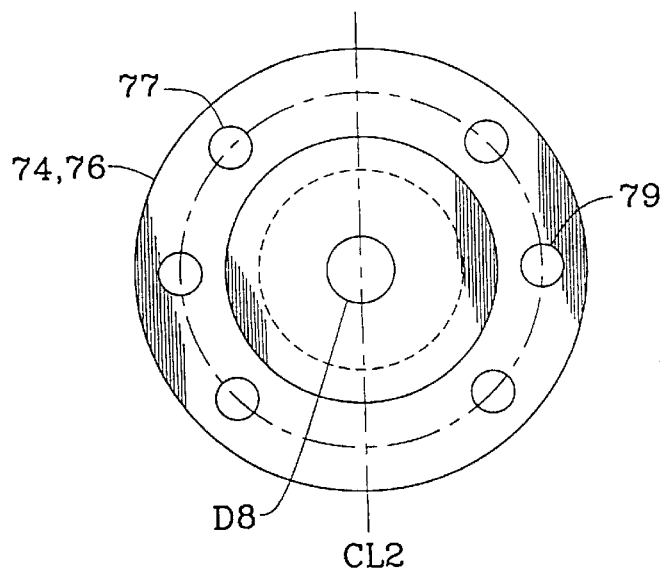
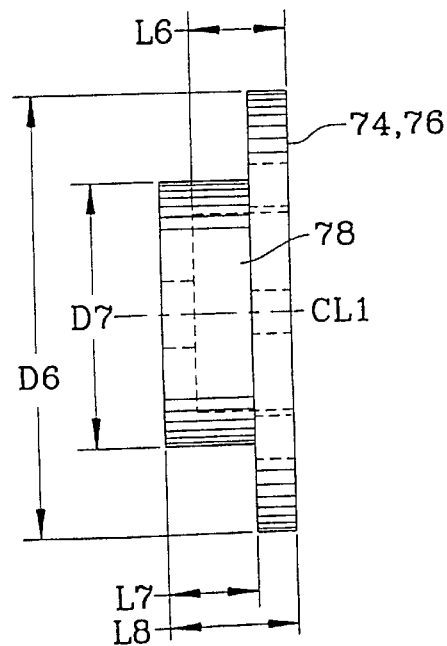

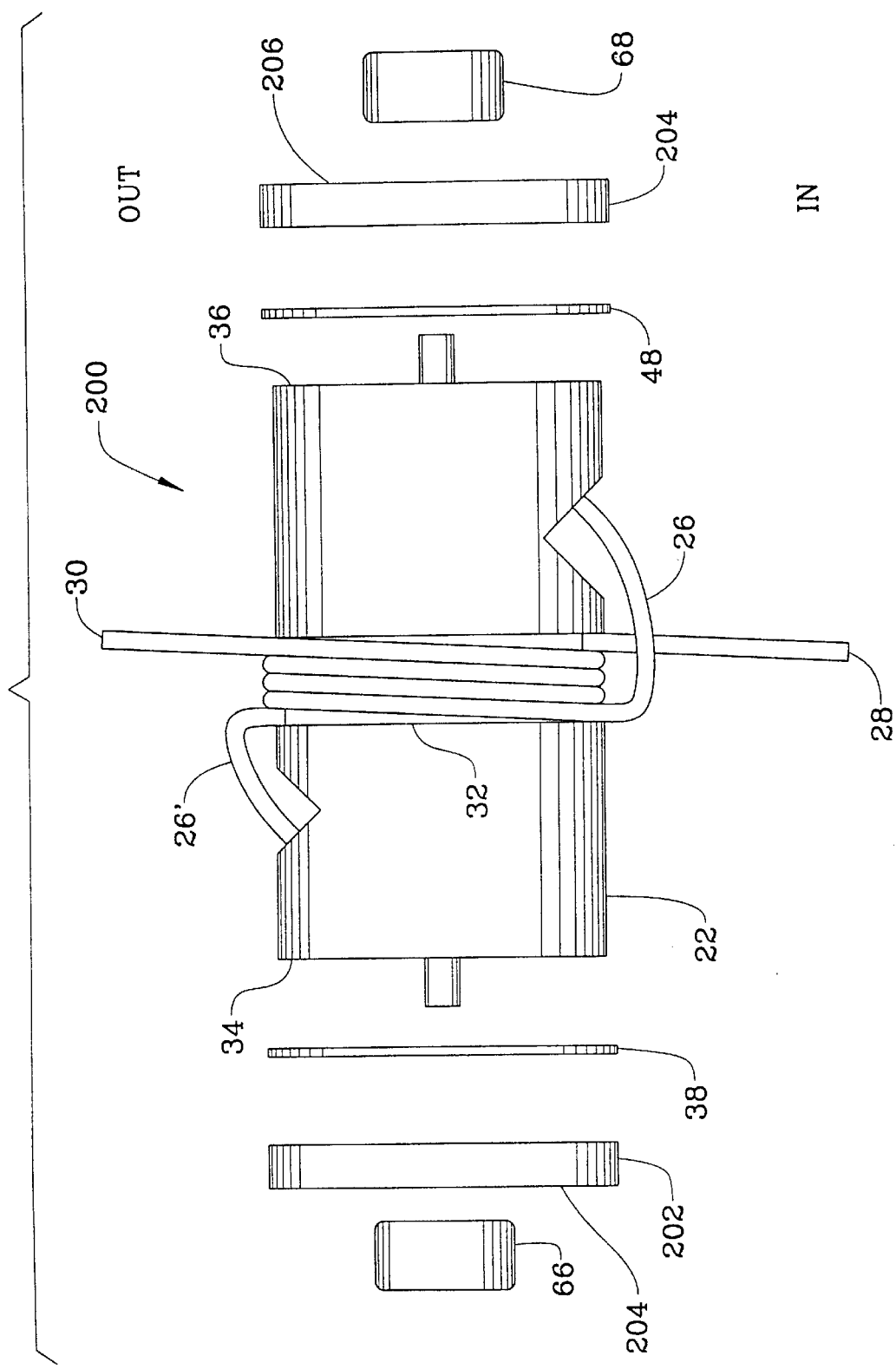

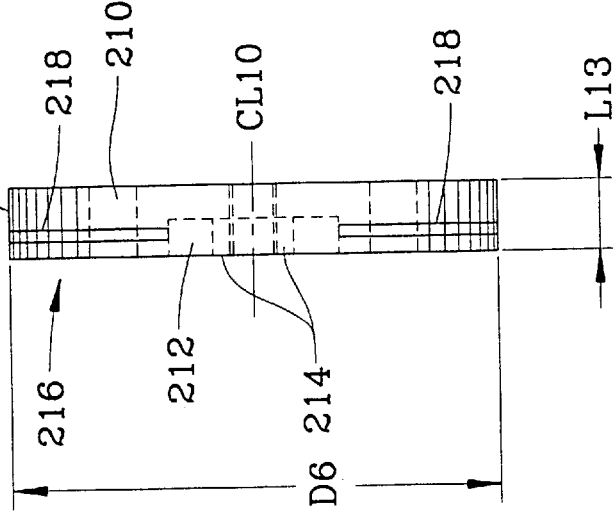
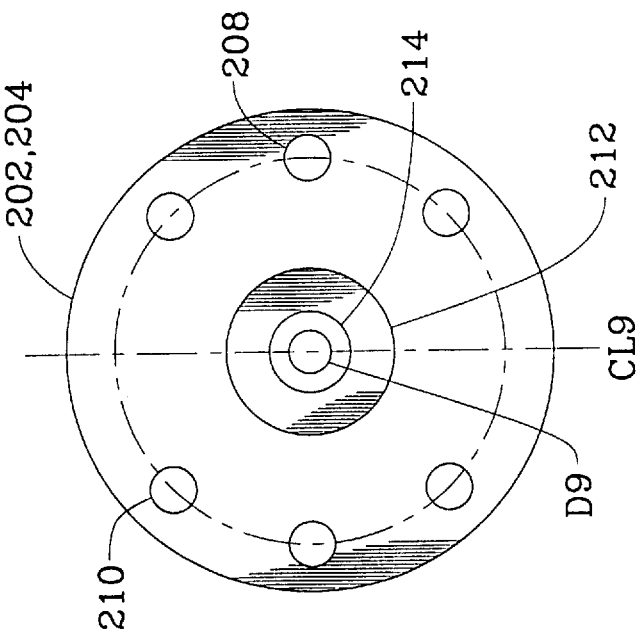
FIG. 2I
FIG. 2H

OPTICAL ACTIVITY DETECTOR FOR USE WITH OPTICALLY ACTIVE COMPOUNDS

This application is a continuation of application Ser. No. 08/594,529 filed on Jan. 31, 1996, now abandoned.

FIELD OF THE INVENTION

This invention relates to an optical rotation detection device and more particularly to an optical detection system for use in measuring optical activity within a sample as it flows through a detector consisting of a laser diode with a beam shaping means, a polarizing prism, a flow cell, and a means for attenuating laser fluctuation effects from the sensed signal.

BACKGROUND OF THE INVENTION

Chemical species called chiral compounds appear in two subtly different molecular forms. These molecular forms are referred to as dextrorotatory and levorotatory, because they cause the plane of polarization of light passing through them to rotate clockwise (or to the right) for dextrorotatory and counterclockwise (or to the left) for levorotatory. The amount of rotation is proportional to the specific rotation of the particular chemical and the optical path length of interaction between the polarized light and the chemical. The geometric shape and relative positions of the constituent atoms for the two types of chiral molecules are generally thought to be mirror images of each other. As such, they have the same chemical composition and are difficult to differentiate. Unfortunately, these two molecular forms can effect human physiology in rather different ways. In extreme cases, patients have been harmed or have died as a result of ingesting a drug that contained too much of the wrong type of chiral molecule.

The enantiomeric ratio is the ratio of dextrorotatory molecules to levorotatory molecules in a particular chiral compound. In less severe cases, patients have failed to respond favorably to drug treatment because the drug they ingested had an undesirable enantiomeric ratio. Simply stated, depending on the particular chiral drug and enantiomeric ratio of that specific batch of chiral drug, and to some extent the particular patient, ingesting a chiral drug may not have the desired positive effect and may have a very negative effect. Such results are especially alarming because, at present, there is no cost effective way to measure and control the enantiomeric ratio of a particular chiral drug.

U.S. Pat. No. 4,498,774 discloses a liquid chromatography detector using a gas laser as a radiation source. This high power radiation source is employed to give a very high ultimate signal-to-noise ratio (S/N). To use this power to its full advantage, very high quality prism pairs are needed to give an extinction ratio of around $10^{+10}$. These prism pairs are hand selected by trial and error techniques and, as such, turn out to be very expensive when the cost of labor is factored in. Typically it might take 5–25 hours to hand select and find the highest quality area to use on any given prism. Additionally, an intensity stabilization unit is used on the laser output to reduce the flicker noise contribution. To retain the high extinction ratio, air-based modulators are used. Such air-based modulators use a great deal of current and hence require added cooling sources to the power source and the modulator units. This patent was issued on Feb. 12, 1985 and has since been abandoned. This patent is hereby incorporated by reference, with various improvements submitted herein.

U.S. Pat. No. 5,012,101 discloses an optical-rotation detector which employs various principles of U.S. Pat. No. 4,498,774, but instead utilizes a laser diode for improved stability and S/N ratio. A modulation means is used to produce a carrier wave by modulating the rotation of the polarization from a radiation source. Optically active samples in the beam path produce a detectable amplitude modulation in the carrier signal. However, since the overall amplitude modulation can be quite small, improvements in the sensitivity of detection schemes are needed.

Additionally, systems need to be more robust for easier set up, construction, and generalized high volume end use. Such enhancements would come through the improved construction of such elements as the flow cell to reduce factors causing depolarization or misalignment. Other improvements might include the machining of the system parts into shapes which can be easily precision interfaced so that they can be interchanged with minimal mounting fixture adjustments. Moreover, the detection scheme could include multiple sensors and compensation circuitry to eliminate the effect of power fluctuations in the laser source.

SUMMARY OF THE INVENTION

The instant invention is an improvement upon the prior art in that an optical rotation detector is provided that is more compact, more robust, and generally easier to set up and operate than previous systems. Unlike prior systems, the present system uses a diode laser whereby the beam is first passed through a length of fiber optic cable to first insure a near-gaussian beam. Alternatively, the laser might have a cylindrical focusing lens attached directly to the emitting aperture of the laser diode, underneath the hermetically sealed window.

Next, the system employs a glan-Thompson prism to improve the linear polarization ratio of the laser output, but unlike previous systems the prisms need not be hand selected as described above. Also unlike prior systems, a Faraday rotator is used which consists of a rod of Terbium Gallium Garnet (TGG) placed inside a solenoid. The polarization of the beam is then varied according to a reference oscillator frequency (f). This TGG modulator uses significantly less current than other Faraday rotators (e.g., air core) as suggested by the prior art.

Additional improvements include a specially constructed flow cell, with improved construction and sealing techniques, for allowing the beam to pass through a sample substance with minimal reflection or dispersion. The sample substance alters the angle of the plane of polarization of the beam if the sample is optically active and this results in a periodic amplitude variation in the detected signal. To further enhance detection of this amplitude variation, the present invention attenuates (or subtracts and filters out), via low cost circuitry, laser amplitude fluctuations and the 2f signals relative to the desired amplitude modulated f frequency signal to be detected. This allows for greater resolution in detection of chiral compounds with the present invention which is immune to laser fluctuations.

To date, this invention has been used as a detector in a High Performance Liquid Chromatography (HPLC) system. In a typical HPLC system a liquid sample is injected into a high pressure solvent stream and is subsequently forced through a tightly packed column. A column consists of a cylindrical pressure vessel usually packed with very small spheres of silica, where the silica are often coated. Because of variances in chemical attraction between the different types of molecules in the sample and the column packing material, and in the presence of the proper solvents, the different chemical molecules of the sample elute from the column separated in time.

HPLC is a separation technique that can present separated chemical species from the sample to downstream detectors one at a time. Thus, one can measure various physical parameters (absorbance of light at various wavelengths, refractive index, conductivity, optical rotation, etc.) of each constituent in a sample as that constituent flows through a flow cell in the detector. Typically, each detector has its own flow cell and measures only one type of physical parameter. It is common also to have two or more detectors/flow cells in series in order to better quantify the sample being measured.

A typical system using HPLC and the present invention would separate the sample and, for each elutant, measure the optical absorbance with an optical absorbance detector to determine the total amount of each sample constituent eluted. Then, an optical rotation detector as described by the present invention would be used to determine the net optical rotation. Knowing the specific rotation of the elutants, one can calculate the enantiomeric ratio. This general procedure is typical of analytical systems used in research and quality control.

Alternatively, if a special chiral separation column is used to separate the enantiomers, the present invention might be used to identify the direction of optical rotation and thus to identify the enantiomer. This approach is typical of preparative applications used to collect and/or concentrate a desire enantiomer. Additionally, process control systems might use the present invention to aid in optimizing conditions for production of the preferred enantiomer. Conversely, the present detector might be used to minimize production of unwanted enantiomers.

In general practice, the analytical applications are the most difficult and stressing on instrument design because they require a small flow cell volume, and yet must have enough sensitivity to detect very dilute samples. Preparative and process control applications typically use much larger flow cell volumes and usually have the advantage of much higher concentrations of sample. The present invention provides a detector capable of being readily used in any one of these suggested applications.

Hence, the present invention is an optical instrument that passes a narrow beam of laser light through the long narrow bore of a flow cell. Analytical applications (for instance) might typically use a flow cell having an inside diameter of 0.030 inches and length of 2 inches. After passing through the glan-Thompson prism, the beam has a high degree of linear polarization (typically 100,000:1). The flow cell is configured so as to continuously flow liquid through the same long narrow bore, thus allowing the liquid and beam to interact. The rotation of the plane of linear polarization of the beam is measured as liquid flows through the bore of the flow cell. The rotation due to the flow of sample through the flow cell is typically much less than +/– one degree. Given the disclosed techniques of the present invention, a precise measurement of a sample can be made approximately 30–45 minutes after the detector has been delivered and turned on. With previous systems, the typical time needed from turn on to sampling is upwards of 25 hours in order to make all the necessary alignments and adjustments.

Accordingly, it is an object of the present invention to provide an improved optical rotation detector, particularly for use in detecting, separating, and measuring enantiomeric ratios of chiral compounds and/or related pharmaceutical drugs in high performance systems.

It is a related object of the present invention to provide an improved optical detector which utilizes a length of optical fiber or a lens for conditioning a laser diode beam to be near-gaussian in distribution.

It is yet another object of the present invention to provide an improved optical detector with an improved flow cell for passing the laser beam through chiral substances with minimal mechanical birefringence.

It is still another object of the present invention to provide an improved optical detector with compensation circuitry which detects the reflected photodetector signal and subtracts it from the primary photodetector signal to leave a resulting amplitude modulation signal with greater detectable resolution and resistance to laser fluctuations.

It is yet another object of the present invention to provide an improved optical detector with flow cell and mounting block parts that have been machined to be more easily interchangeable with no significant loss of alignment integrity.

It is a related object of the present invention to provide an improved optical detector which can be setup and used in significantly less time than prior systems.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 2C is an end view of the sealing washer from the flow cell.

FIG. 2D is an end view of the donut shaped end washer from the flow cell.

FIG. 2E is an end view of the endcap of the flow cell.

FIG. 2F is a side view of the endcap of the flow cell.

FIG. 2G is yet another embodiment of the flow cell with an alternative arrangement for mounting the windows.

FIG. 2H is an end view of the endcap used for the flow cell of FIG. 2G.

FIG. 2I is a side view of the endcap of FIG. 2H.

DETAILED DESCRIPTION OF THE PREFERRED EMBODIMENT

Although the invention is described in terms of a preferred specific embodiment, it will be readily apparent to those skilled in this art that various modifications, rearrangements and substitutions can be made without departing from the spirit of the invention. The scope of the invention is defined by the claims appended hereto.

Figure 1:
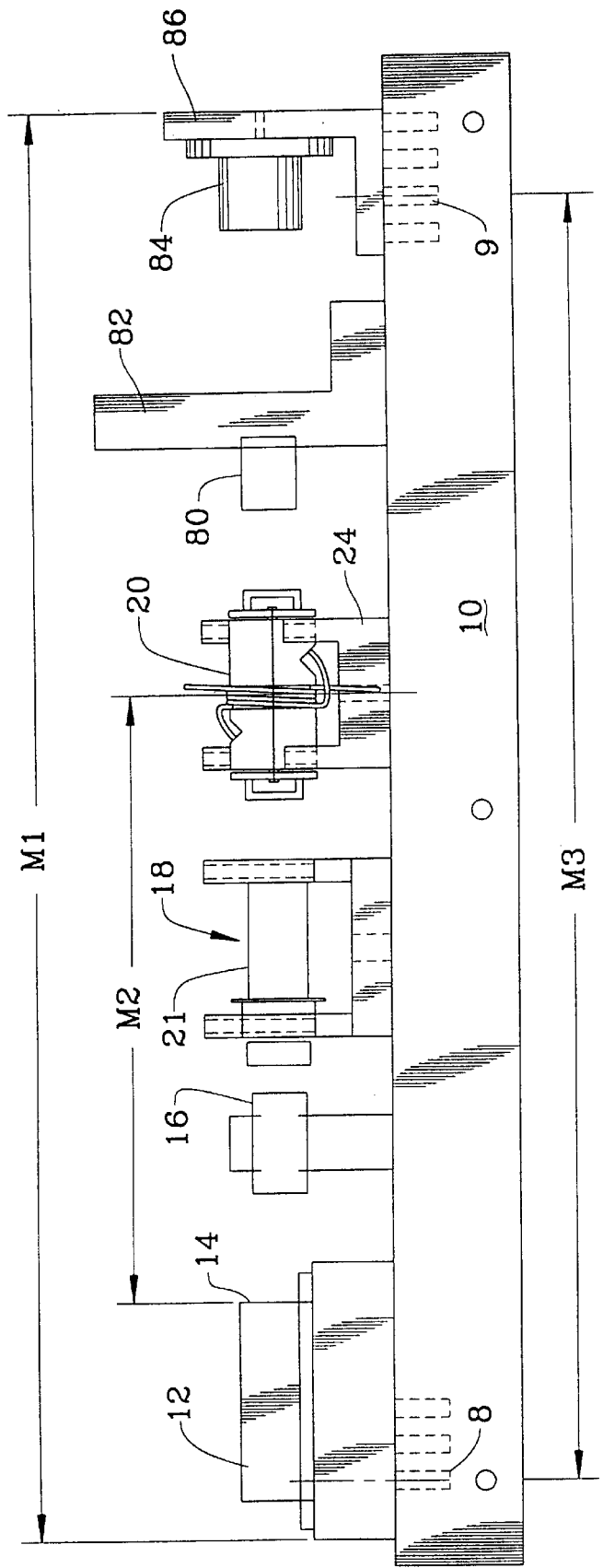
FIG. 1 is a side view of an optical rotation detector setup showing the bench and mounts with the laser, first prism, Faraday rotator, flow cell, second prism, and detector.

Referring now to FIG. 1, an optical bench 10 is shown which rigidly supports the various components of the detector assembly and is typically made from solid aluminum. Once the various mounts for the components are in place they are generally not to be readjusted by the user (e.g. laser, prisms, detector). Prior systems allowed for too much adjustability and systems were often knocked out of alignment. The flow cell is unique in that it is often changed and/or cleaned and interchangability is a necessary design feature without the user having to realign the entire bench after the cell is remounted. The present system offers significant advantages in that a complete system can be constructed, shimmed, and aligned in much less time than previously disclosed systems. The overall length M1 of the mounted components is 18.91 inches. Length M2 of 7.874 inches (200 mm) shows the focal length of the laser assembly. Length M3 of 17.000 inches shows the length between mounting holes 8 and 9.

The detector assembly includes a laser unit 12 which contains a visible laser diode which typically operates at a wavelength of 690 nanometers with a power output of 10 milliwatts. The laser diode is coupled to a length of single mode optical fiber (not shown), typically 2 meters in length. The output of the optical fiber is coupled to a focusing lens 14 which is used for bringing the beam to focus inside the flow cell 20. This arrangement is used because the output of a laser diode is generally astigmatic and asymmetric in both divergence angle and shape. After traveling the length of the optical fiber, however, the beam is substantially uniformly symmetric and non-astigmatic and can be focused into a well defined near-gaussian beam.

An alternative method of achieving a satisfactory beam shape is to place a cylindrical lens under the hermetically sealed window and directly on the emitting aperture of the laser diode. Another method involves the use of multiple lenses and prisms to achieve a near-gaussian beam. Beam shape is important because any portion of the beam that is reflected from the walls of the flow cell, for example, becomes depolarized and adds to the system noise. Thus for maximum sensitivity, it is important that almost all of the laser beam pass through the flow cell without reflection.

Figure 3A:
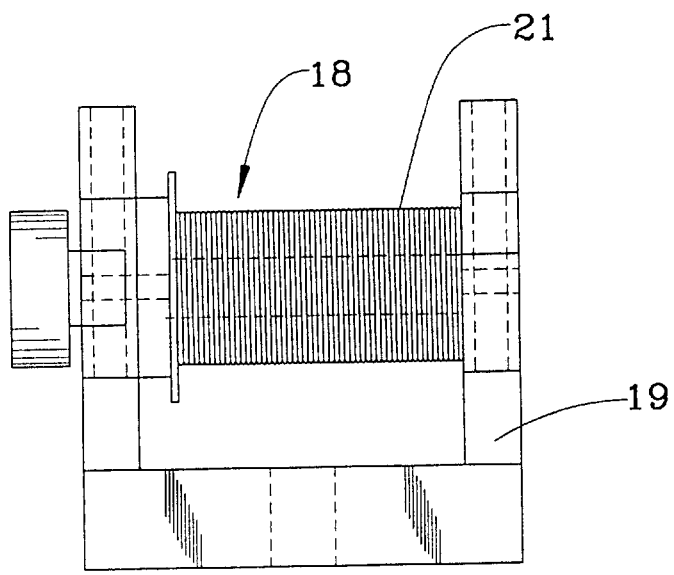
FIG. 3A is a side view of a Faraday rotator in its mounting fixture.
Figure 3B:
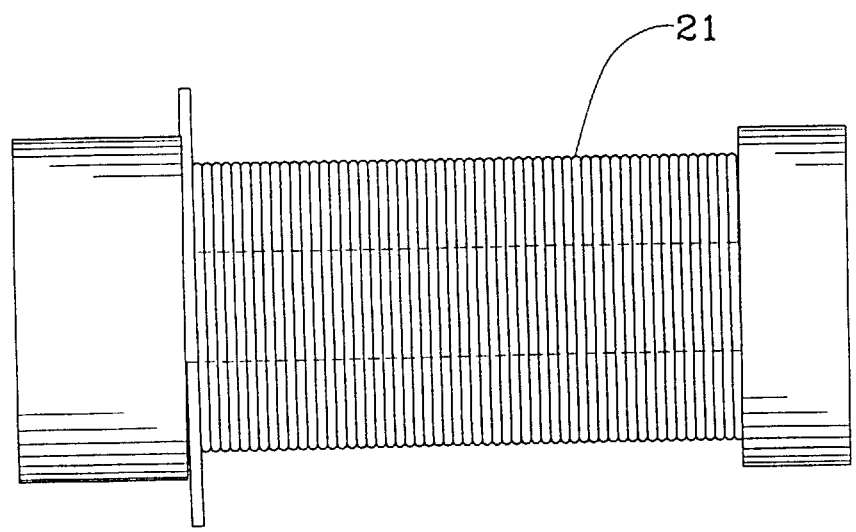
FIG. 3B is a side view of a Faraday rotator showing the wound solenoid core.

A glan-Thompson prism 16 is used to improve the linear polarization ratio of the laser output from 100:1 to 100,000:1. A Faraday rotator 18 is used to rotate the plane of polarization about the longitudinal axis of the rotator, which is coaxial with the laser beam. FIG. 3A shows the Faraday rotator 18 on its mount 19 which fixes the rotator to the optical bench 10. The Faraday rotator consists of a rod of Terbium Gallium Garnet (TGG), typically 5 millimeters in diameter and 30 millimeters long, placed inside a solenoid. Referring to FIG. 3B, the solenoid 21 typically is comprised of 4000 turns of #30 magnet wire uniformly wound on a non-magnetic spool (e.g. Delrin) of length 40 millimeters and inside wire diameter of 7 millimeters. The solenoid of the Faraday rotator is driven by a sine wave from a reference oscillator (see FIG. 5) at a frequency f (typically 500 Hz)

Figure 2:
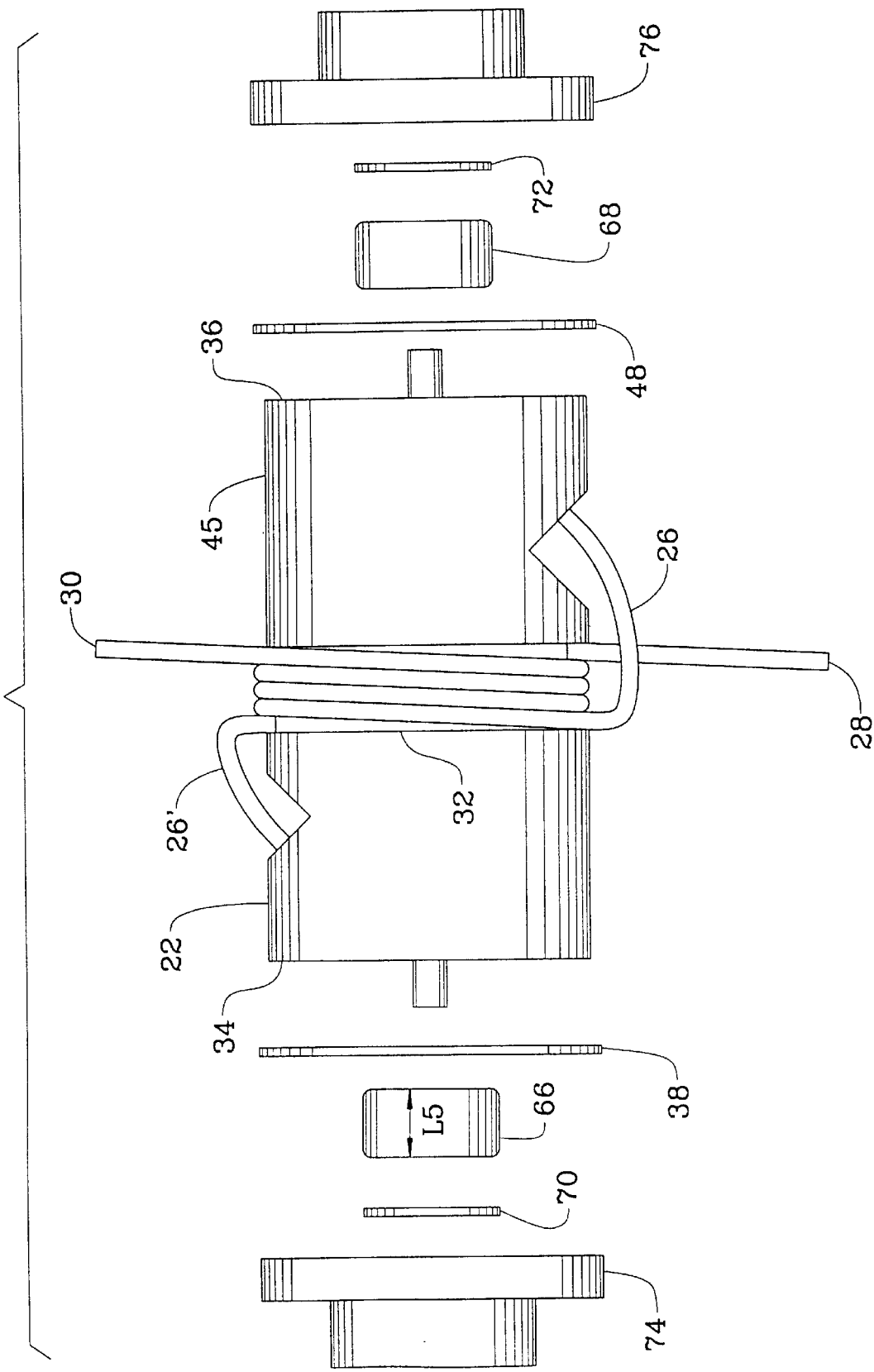
FIG. 2 is an exploded side view of a flow cell assembly.

Referring now to FIG. 2, the flow cell 20 (in FIG. 1) is shown in exploded fashion. As stated, the flow cell is used to direct the solvent and sample flow through the linearly polarized beam. The flow cell body 22 of the flow cell 20 typically consists of 316 stainless steel and the body is engineered to fit in a "V" block mount (see FIG. 4). Of course, other suitable materials might be used. In particular, the flow cell body 22 and the mount 24 are precision machined so that different flow cells can be used on the same "V" block without realignment. Given that cylindrical lathing is a very precise operation, and the formation of a "V" mount can be similarly precise, these two shapes used together create a unique interface which allows such interchangability without realignment. This is an extremely important feature for the flow cell mount because the flow cell might need to be removed and cleaned periodically, or replaced altogether. In prior disclosed systems, a difficult realignment process occurs every time a flow cell is replaced or removed for cleaning.

Figure 2B:
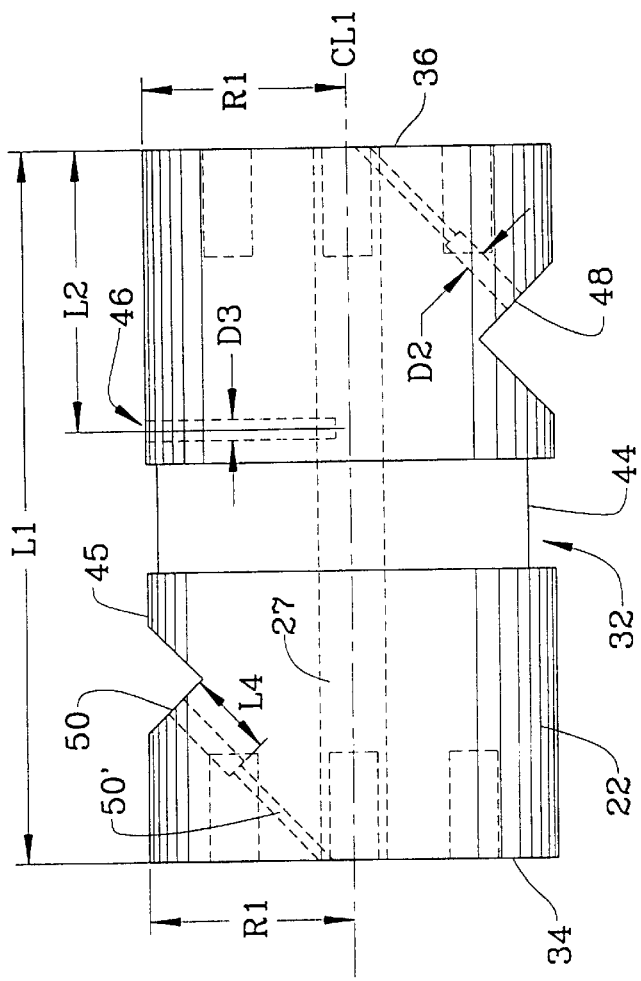
FIG. 2B is a side view of the flow cell body.
Figure 2A:
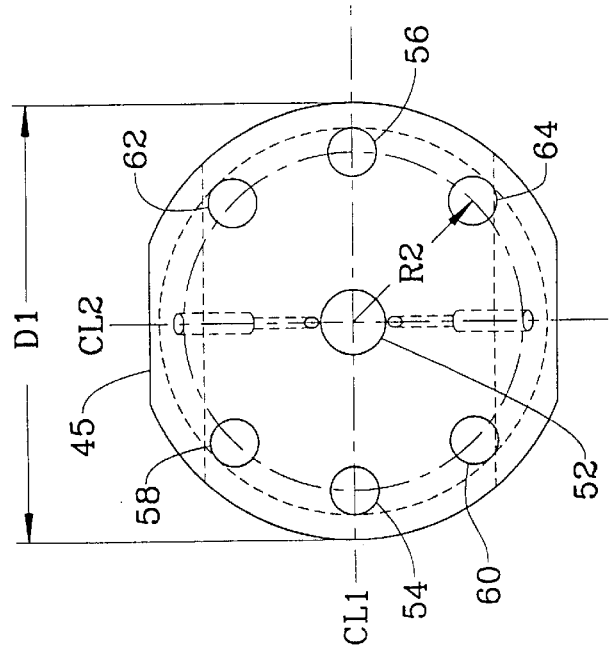
FIG. 2A is an end view of the flow cell body.

Referring now to FIGS. 2A and 2B, various dimensions as used in the flow cell of this embodiment are shown. The flow cell body length L1 measures 1.969 with a tolerance of +/- 0.050 inches after assembly and grinding. The distance R1 measures 0.550 inches from the centerline 1 (CL1) . The largest diameter D1 of the flow cell measures 1.2000 inches. A glue hole 46 (see flow cell assembly details below) is located 0.73 inches from end 34 with a diameter D3 of 0.05 inches. A flat cutout 45 runs along the top of the flow cell body 22 from end 34 to end 36. As shown below, this flat cutout allows a top cross member to be placed over the flow cell to hold it in place on its mount.

The end view 2A of the flow cell shows a 0.177 inch through hole 52 which runs the length of the flow cell body 22. Additionally, two partial alignment holes 54, 56 are shown (180 degrees apart along CL1) with a nominal diameter of 0.125 inches, 0.3 inches deep, and centered a radius R2 of 0.950 inches from the center of the flow cell. Four other partial through holes 58, 60, 62, and 64, are used for attachment screws, are each 45 degrees from centerlines CL1 and CL2, threaded #4-40×0.3 inches deep and centered along radius R2 of 0.950 inches from center.

Referring again to FIGS. 2, 2A, and 2B, a length of fused quartz capillary tube 27 (4 mm outside diameter OD×0.75 mm inside diameter ID) is shown cemented in the center of the flow cell body with epoxy. This thick capillary tube in the main bore reduces scattering and subsequent depolarization because those portions of the laser beam that do not travel through the bore (e.g. the portion of the beam that hits the solid portions of the fused quartz capillary tube) are less likely to scatter into the detector. Less scattering of the beam leads directly to lower system noise.

Additionally, an inlet tube 26, as well as an outlet tube 26', is wrapped around a groove 44 in the flow cell body 22. In this embodiment, the groove measures 0.40 inches wide and 0.07 inches deep. The depth and width of this groove might vary with the amount of tubing desired for the particular application. Inlet tube 26 terminates in an inlet port 28 and outlet tube 26' terminates in outlet port 30.

Additionally, ports are drilled at each end 34 and 36 of the flow cell body 22. The port holes 48' and 50' start just outside the fused quartz capillary tube 27 and continue into and radially out of the body at 45 degrees to the longitudinal axis exiting the flow cell at countersink holes 48 (input) and 50 (output). Putting the inlet port 28 (entering the cell at point 48) on the bottom and the outlet port 30 (exiting the cell at countersink hole 50) on the top makes it easier to flush the cell of gas (e.g. air) bubbles. Additionally, each 45 degree port hole 48', 50' is counterbored from the outside diameter of the flow cell body 22 to accept tubes 26, 26'. The preferred embodiment for analytical applications uses ¹/₁₆ inch outside diameter tubing with a 0.010 inch inside diameter for the inlet tube 26 and 0.030 inch inside diameter for the outlet tube 26'. The 45 degree port holes 48' and 50' are drilled through with a diameter of 0.030 inches and countersunk a length L4 of 0.25 inches deep with a diameter D2 of 0.062 inches.

The tubing 26, 26' is wrapped around the midsection 32 of the body and brazed at the counterbores of the 45 degree port holes 48', 50' and the midsection 32. The wrapping and brazing around the midsection greatly reduce temperature gradients within the flow cell 20. Each flow cell end 34 and 36 is covered with a sealing washer 38 and 48. These washers might be made from a variety of materials including chlorotrifluoroethylene (Kel-F), fluorinatedethylenepropylene (FEP), tetrafluororethylene (TFE), or other suitable materials. Referring now to FIG. 2C, each sealing washer has a slot 42 which allows liquid to flow between the central bore of the fused quartz capillary tube and the inlet or outlet port. In this embodiment, the slot measures 0.190 inches in height, 0.060 inches in width, and has a radius on the ends of 0.030 inches. Additionally, each sealing washer 38, 48 is 0.030 inches thick and has a set of alignment holes 55 (two) and screw holes 59 (four) corresponding to the holes 58–64 in the flow cell body 22.

Referring again to FIG. 2, each sealing washer is covered by an optical window 66, 68. In this embodiment, this cylindrical window is 0.492 inches in diameter and has a length L5 of 0.236 inches. It is made from synthetic fused silica with 5 arc parallelism and AR V-Coat at 680 nm (reflectivity<0.5% from 670 to 690 nm—one side only). Such materials can be obtained from such laboratory supply sources as Melles Griot of Irvine, Calif.

Each window is retained by an endcap 74 and 76 with a length L8 of 0.335 inches. As shown in FIGS. 2E and 2F, each endcap also has a set of alignment holes 79 (two) and screw holes 77 (four) which correspond with holes 58–64 of the flow cell body 22 and sealing washers 38, 48. The endcap has an outer diameter D6 of 1.200 inches and a through hole with diameter D8 of 0.200 inches. The endcap steps down to a section with a length L7 of 0.235 inches and a diameter D7 of 0.700 inches. Additionally, the endcap has an inner cylindrical cavity 78 facing the flow cell with a diameter of 0.500 inches and a depth L6 of 0.245 inches for receiving the protruding end of the optical window. Typically, this endcap is made from polyetheretherketone (PEEK). Other suitable materials could similarly be used.

As shown in FIGS. 2 and 2D, a donut shaped end washer 70, 72 is placed between each endcap 74, 76 and each optical window 66, 68. As with the previous washers, these washers are also made from materials such as chlorotrifluoroethylene (Kel-F), fluorinated ethylene propylene (FEP), tetrafluororethylene (TFE), or other suitable materials. In this embodiment, the washer is 0.020 inches thick and has an outer diameter D4 of 0.490 inches and an inner hole with a diameter D5 of 0.200 inches.

While such end washers are shown in this embodiment, they are not required. One reason for including them is to provide a smooth surface for contacting the optical window 66, 68 and hence minimize induced bimechanical refringence. In general, it is more difficult to smooth the inside contacting surface of the endcap as opposed to forming the end washer from an already relatively smooth material. Hence a washer can be used to provide a smooth contacting surface (as shown in FIG. 2), or alternatively the flow cell can be constructed without the end washer provided the inside surface of the endcap has been sufficiently machined or smoothed.

Referring now to FIG. 2G, an alternative arrangement of the flow cell is shown. In this embodiment, the flow cell 200 utilizes, as before, inlet tube 26 and outlet tube 26' wrapped alternately around central cutout 32. Inlet tube 26 enters the cell at the bottom has at its other end input port 28. Outlet tube 26' exits the cell at the top and has at its other end output port 30. Again, this embodiment uses sealing washers 38 and 48 over the ends of the cell body 22. The optical windows 66 and 68, however, are mounted differently onto the flow cell. A different form of endcap 202, 204 is used wherein the endcap mounts directly onto sealing washers 38, 48 with no receiving cavity 78 for the optical window. The windows 66, 68 are instead adhered directly to the outside ends 204, 206 of the endcaps.

Referring also to FIGS. 2H and 2I, a front and side view of endcaps 202, 204 are shown. Each endcap has a diameter D6 of 1.200 inches and a length L13 of 0.200 inches. As shown, each endcap also has a set of alignment holes 208 (two) and screw holes 210 (four) which correspond with holes 58–64 of the flow cell body 22 and sealing washers 38, 48. The center through hole has a diameter D9 of 0.100 inches. On the outward facing side 216 of the endcap, a cylindrical mote 212 has been formed which has an outside diameter of 0.40 inches and an inside diameter of 0.20 inches, and is 0.10 inches deep. A donut-shaped island 214 then exists around the center hole with an outside diameter of 0.20 inches.

To mount the optical window, the window is clamped over the mote and flush against the side 216. The mote 212 is then filled with silicone adhesive via a glue holes 218 which penetrate the side of the endcap 202, 204 and enter the mote 212. In practice, glue might be injected into one hole until the mote fills and the glue exits the other hole. The outer diameter of the window 66, 68 is slightly larger than the outside diameter of the mote. The window then mounts against the donut shaped island 214, with the adhesive contacting the window along the mote. When the adhesive dries, it shrinks and draws the window tightly and securely against the island 214. This mounting technique is advantageous in that no external stressing forces are placed upon the optical window to cause mechanical birefringence and misalignment. However, it is particularly important with this arrangement to thoroughly rinse the flow cell after use to prevent buildup which might possibly crystalize and loosen the mounted window.

Figure 4:
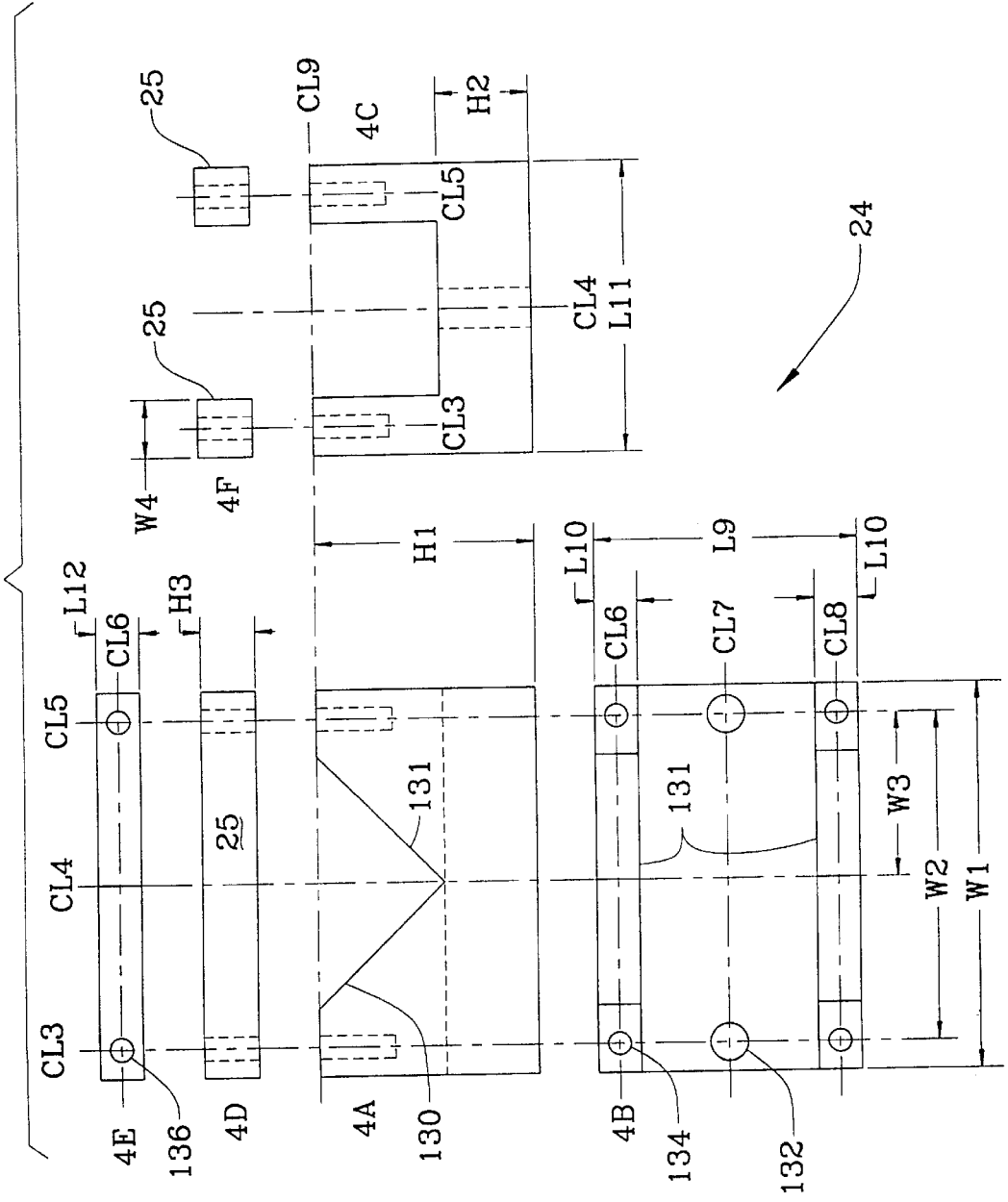
FIG. 4 (4A–4F) is an engineering drawing showing the front (4A), top (4B), and side (4C) views of a V-block mounting fixture, and the front (4D), top (4E), and sides (4F) of the top mounting bar for holding the flow cell on the mounting fixture.

Referring now to FIG. 4, an example "V" mount 24 is shown with its top, front, bottom, and side projected views. For this embodiment, the "V" block is precision formed from 316 stainless steel. Both "V" sections in the center 131 are oriented at 45 degrees on each side and should be precision ground to place the center of the flow cell body—at its 1.2000 outside diameter points—at a height H1 of 1.570+/−0.001 inches above the bottom of the mount. Only the areas where the "V"'s contact the 1.2000 outside diameter of the flow cell body are important. For example, the bottom of the "V"'s do not need to be machined.

FIG. 4A shows the front view of the "V" mount 24 of height H1. The top view 4B shows the alignment and mounting holes 132 (two) along CL4 and CL7, each alignment and mounting hole 132 having a diameter of 0.280 inches. These holes are used to fasten the "V" mount 24 to optical bench 10 with ¼-20 socket head cap screws. Four screw holes 134 along CL3, CL5, CL6, and CL8 are drilled 0.5 inches deep for receiving #8-32 screws. The length L9 of the mount is 1.90 inches with each "V" block measuring a length L10 of 0.30 inches. The mount has a width W1 of 2.70 inches, with the screw holes 134 centered about a width W2 of 2.250 inches. Accordingly, each screw hole 134 is 1.125 inches from CL4. FIG. 4C shows the front view of the mount with length L11 of 1.90 inches and height H2 of 0.70 inches. A top mounting bar 25 is shown in FIGS. 4D, 4E, and 4F which fits over the top and clamps down on the mounted flow cell. Two through holes 136, along CL3, CL5 and CL6 and having a diameter 0.177 inches, allow screws to penetrate the top bar and screw into the screw holes 134 in the mount 24. The top bar has dimensions H3=0.40 inches, L12=0.30 inches, and W4=0.30 inches. As shown this mounting fixture incorporates two spaced apart "V"-blocks, with each using a separate top mounting bar.

The embodied flow cell and mount configuration is beneficial because it has been found that mechanically induced birefringence can cause excessive system noise if the window is stressed. In other words, mechanical stresses in assembling the flow cell can cause the beam to become depolarized and this shows up as detected noise. With the disclosed pieces, the flow cell might be assembled as follows to reduce or eliminate such birefringence problems:

(1) Machine the flow cell body 22, but do not grind the end faces until all steps are complete;

(2) Wrap inlet tube 26 and outlet tube 26' around the flow cell body 22 in the groove 44. The tubes should be wrapped so that they alternate inlet/outlet/inlet/outlet along the length of the body. Each tube should lay snugly against the contour and complete at least 1.5 wraps. Each tube should then be close dressed into the appropriate countersink hole 48, 50. Again, as noted, the inlet is on the side opposite the flat cutout 45, and the outlet is adjacent the flat cutout;

(3) Stainless steel tubing should be brazed at both countersink holes and at the wraps in the groove, with appropriate measures being taken to avoid plugging the tube ends during brazing. After brazing is complete, the assembler should confirm that the tubing ends are not plugged;

(4) Position a length of fused quartz capillary tube (0.75 mm ID×4 mm inch OD) inside the flow cell body 22 such that the tube inside diameter is centered within the 1.2000 outside diameter of flow cell body 22 to within +/−0.001 inches. This can be more easily accomplished by using a "V" block fixture to support the body and tapered pins to support each protruding end of the fused quartz capillary tube;

(5) Cover all exposed holes and cement the glass lined capillary tube inside the body by forcing epoxy through the glue hole 46 until excess epoxy drips out both ends and all internal voids are filled;

(6) When the epoxy has fully cured, grind both end faces of the body until they are smooth, perpendicular to the glass lined capillary tube axis, and the 0.030 through holes break out with a gap of 0.008 +/−0.004 inches from the epoxy ring surrounding the glass lined capillary tube;

(7) Press in four locating or alignment pins (0.125 inches in diameter and 0.5 inches long) so that each protrudes 0.2 inches from the face of the endcaps. The endcap and sealing washer are aligned and the endcap is then retained in position with four #4-40 screws.

Other window retaining schemes have been tried, including the alternative arrangement shown in FIG. 2G. While this alternative arrangement has certain advantages (e.g. low mechanical birefringence), such schemes do not prove as robust as the primary embodiment. Additionally, prior systems fail to properly keep solvents from penetrating the silicone cement located between the window and its mounting surface. As a result, the cement fails and the flow cell leaks. Under the present scheme, leaking problems—as well as mechanical birefringence problems—are minimized.

Referring again to FIG. 1, a second glan-Thompson prism 80 is used as an analyzer and is mounted on the optical bench 10 after the flow cell 20. The mounting fixture 82 holds the prism 80 in fixed alignment with the beam passing through the flow cell 20. The prism 80 is oriented so that its transmission axis is 90 degrees from the transmission axis of the first glan-Thompson prism. As a result, very little light is transmitted by this analyzer prism. The effect of the oscillatory rotation of the Faraday rotator is to rotate the plane of polarization away from the nominal null or minimum transmission condition created when the axis of the two prisms are oriented 90 degrees from each other. The oscillation occurs at a reference frequency f. Such oscillatory rotation is generally small, i.e. less than +/− one degree. Moreover, while operation of the symmetric oscillation about the null or minimum transmission is the usual condition of operation, it has been found that this symmetry is not a requirement for operation.

Light passing through the analyzer components falls on a silicon photodetector 84 positioned in line with the oscillating beam. A mounting fixture 86 holds the detector 84 in a fixed position. Accordingly, the predominant photodetector output signal is amplitude modulated at 2f, or twice the reference oscillator frequency. This occurs because a rotation in either direction by the Faraday rotator causes an increase in light passing through the second glan-Thompson prism 80 and falling on the photodetector 84. This increase in light occurs because the rotation by the Faraday rotator causes the beam polarization to move away from the minimum transmission relationship between the two prism polarizers 16 and 80. When an optically active sample flows through the flow cell, then another—and usually much smaller—modulation component at the reference oscillator frequency f is produced. The amplitude of this modulated signal can be sensed and quantified to indicate the net rotation of the angle of the plane of polarization cause by the sample. Such detection schemes have been generally used in prior disclosures.

Figure 5:
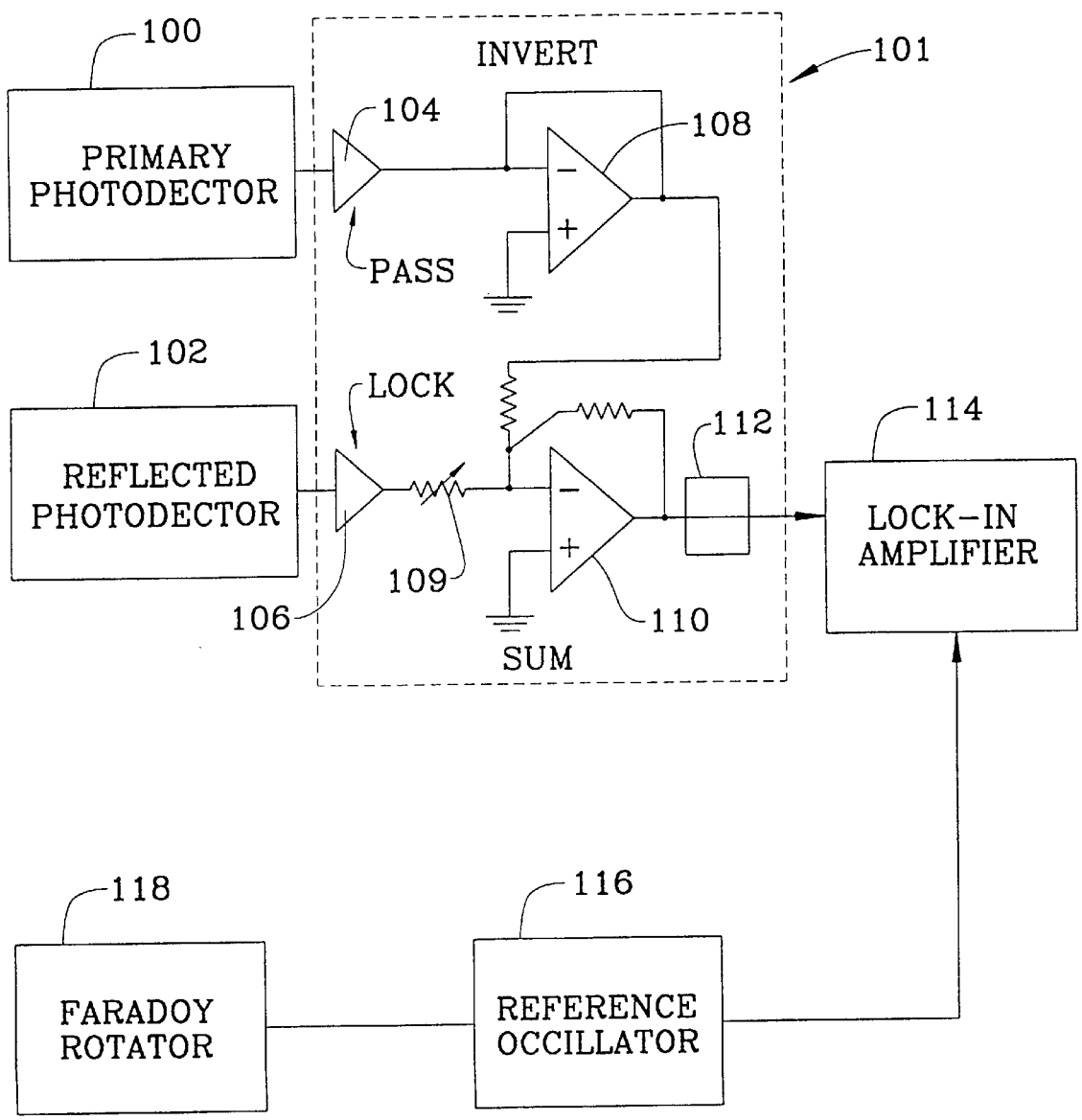
FIG. 5 is an electrical block diagram showing the processing of the detected signal to subtract out the amplitude fluctuations of the laser, and the notch filtering of the 2f frequency signal to enhance resolution and stability against non-sample introduced fluctuations in the measured frequency signal.
Figure 5A:
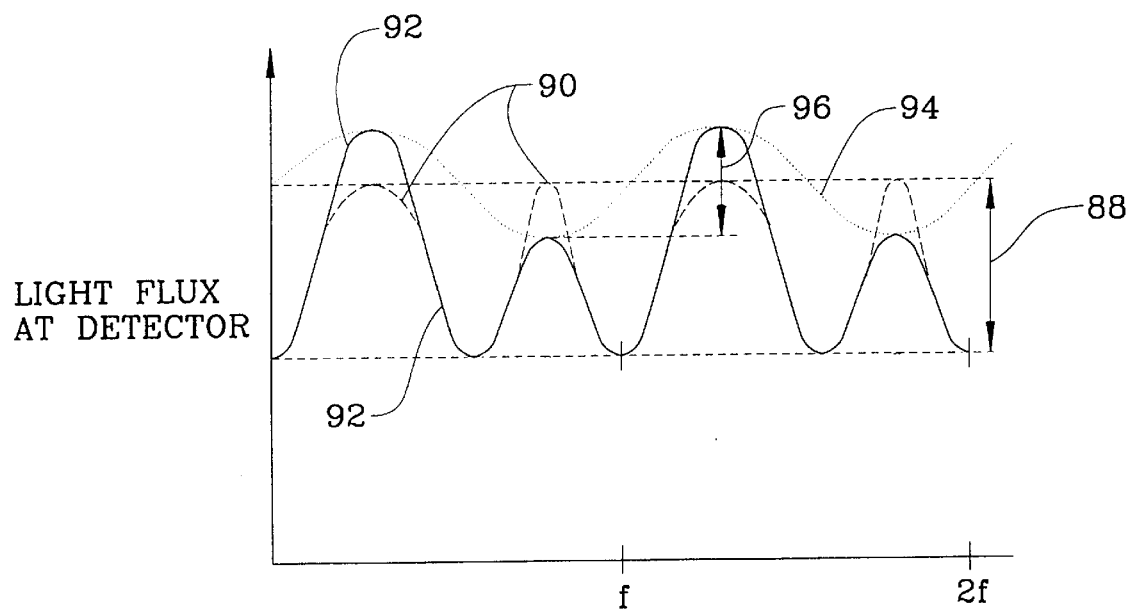
FIG. 5A shows a plot of the amplitude modulated 2f signal, the non-amplitude modulated 2f signal, and the resulting signal resulting from the amplitude modulation at frequency f.

Referring now to the block diagram of FIG. 5, the present invention greatly improves upon the robustness of this detection scheme by introducing a compensator circuit. This circuit requires the placement of a second photodetector (similar or identical to the first) so as to catch light reflected from the entrance of the analyzer prism 80. This reflected beam will not be amplitude modulated by polarization changes caused by an optically active sample flowing through the flow cell 20 and affecting the polarization of the beam, nor by the rotation caused by the Faraday rotator (resembling plot 90 with amplitude range 88 in FIG. 5A). The reflected beam will, however, be modulated by any variation in laser amplitude.

The block diagram shows the compensator circuit 101 and its related processing of the signals. The signal from the primary photodetector 100 (resembling plot 92 in FIG. 5A) and the signal from the reflected photodetector 102 are both fed through active low pass filters 104 and 106. In this embodiment, these filters are implemented using operational amplifier (op-amp) components which first changes the input current to a corresponding voltage and then actively filters the signal, typically with a roll-off frequency of 750 Hz. The low pass filters remove unwanted noise prevalent at higher frequencies and provide some attenuation of the 2f signal.

Compensator circuit 101 also uses op-amps wired as an inverter 108 and as a summing inverter 110 to invert the primary signal and sum the result with the reflected signal. Variable resistor 109 can be adjusted to balance the primary signal and reflected signal so that they evenly cancel out. This can be accomplished during factory adjustment by introducing a modulation into the laser output and adjusting the resistor 109 until a flat signal is detected. This "subtraction" of signals serves to attenuate any amplitude fluctuations that might occur due to laser beam power fluctuations. Since both the primary signal and the reflected signal will correspondingly fluctuate, a subtraction of the two yields a robust signal. This robust signal will show only the amplitude modulation as attributable to an optically active sample flowing through the flow cell and affecting the polarization of the beam.

As an additional measure, a multi-stage active notch filter 112 is used to further attenuate the 2f signal relative to the f signal. This notch filter is similarly comprised of low cost op-amp components. Hence, as a whole, the low cost op-amp compensator circuit 101 (components indicated by dotted the line) is designed to attenuate the influence of laser power fluctuations and also to attenuate the 2f frequency.

The resulting f frequency signal (resembling plot 94 in FIG. 5A, with an amplitude range of 96) is then processed by a lock-in amplifier 114 which is driven by reference oscillator 116. This amplifier, sometimes called a phase sensitive detector, is used to provide a DC output voltage that is linearly proportional to the amplitude and phase modulation at frequency f in this compensated signal. A lock-in amplifier is extremely selective and is primarily affected by the amplitude and phase modulation at exactly the same frequency as the supplied reference oscillator. This reference oscillator is the same device used to drive the Faraday rotator 118 at frequency f. The output from the lock-in amplifier might be used to drive a strip chart recorder pen or a computerized data collection system.

Yet another alternative embodiment would include the use of a compensator circuit, but without the second photodetector 102. In FIG. 5, this would be represented by eliminating elements 102, 106, 108, 109, and 110. As a result, the primary photodetector signal would still pass through the active low pass filter 104 and the active notch filter 112 to attenuate the effect of the 2f signal. Hence, even systems with relatively "quiet" lasers would still benefit from compensator circuitry which attenuates undesired signal components.

Figure 6:
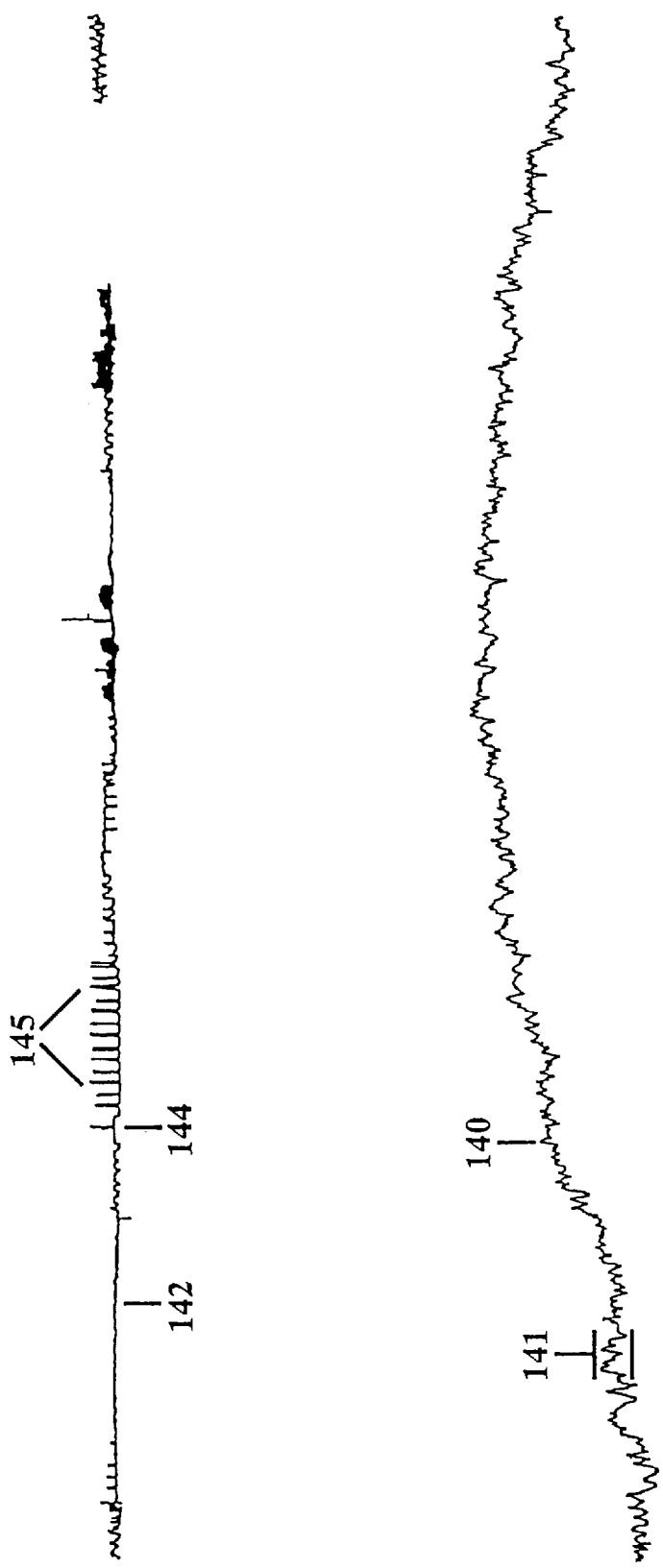
FIG. 6 shows a plot of the lock-in amplifier output versus the laser amplitude, but with the compensator circuit activated which subtracts out the amplitude fluctuations of the laser so that changes in the laser amplitude do not significantly affect the lock-in amplifier results.

Referring now to FIG. 6, an example of the benefits of the compensator circuit are shown. The lock-in amplifier output is plotted 140 in parallel with the laser amplitude 142. As shown, at time 144 the fluctuations in the laser amplitude increase and become more erratic. The relative noise level 141 in signal 140, however, is unaffected by the spikes 145 in the laser amplitude output. If such variations showed up in the signal 140, then the detection limit would be degraded.

Accordingly, the compensator circuit is important because all lasers have "flicker" noise, or short term amplitude variations. Today, it is difficult to build or buy a laser with "flicker" noise that is less than 0.1%. The output of the lock-in amplifier (phase sensitive detector) has been shown to be sensitive to "flicker" noise. In order to achieve a system noise level that is below a few hundred microdegrees of rotation, "flicker" noise must be better than 0.05%, or some means of compensation must be used. This compensation has traditionally been applied to the laser beam. The present invention discloses a technique that removes the "flicker" noise from the signal. The advantages include, for instance, reduced cost and complexity.

In summary, as an optically active sample passes through the flow cell, the output from the lock-in amplifier will deflect from the nominal solvent baseline in a positive or negative direction, depending on the direction and amount of rotation of the plane of polarization due to that sample. The amount and direction of deflection (e.g. 96 in FIG. 5A) of the output from the lock-in amplifier is linearly proportional to the rotation caused by the sample. From this, the presence, and/or amounts, and/or net optical rotations of chiral compounds can be detected. As stated above, such a robust, yet sensitive, detector might be used for analytical, preparative, or process control applications. It is also possible to use an optically active solvent and detect the reduction of rotation caused by a sample that is not optically active. Other analysis or processing scenarios should suggest themselves for the current application at hand.

Figure 7:
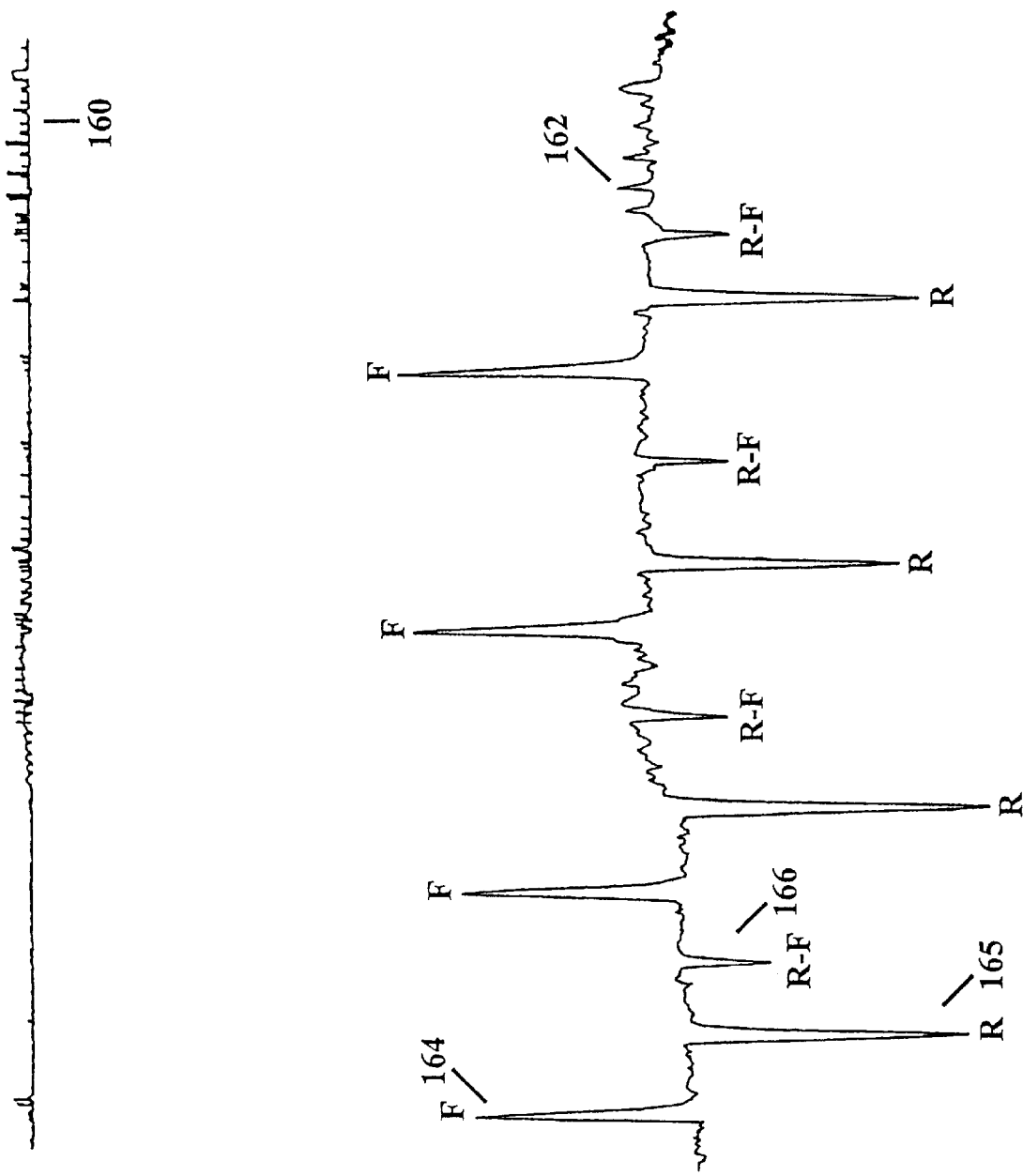
FIG. 7 shows a strip chart recording of the detected results from a sample containing a mixture of optically oriented molecules and the detected results which allow calculation of the true enantiomeric ratio.

FIG. 7 shows an example of the output from the described system. Raffinose (R) and fructose (F) were diluted to a concentration of 0.1 micrograms/microliter and injected directly into the solvent flow just before the flow cell (no column). With a 2 centimeter path length and the stated concentration of 0.1 micrograms/microliter the rotation is +526,000 microdegrees for raffinose and −447,500 microdegrees for fructose. The appropriate peaks are marked R and F. Then a 50:50 mixture of these two solutions was injected and marked R+F. As shown, the resulting peak is equal to the net rotation of 526,000−447,500=78,500 microdegrees. Further the laser amplitude fluctuations, indicated on the upper trace 160, did not unduly affect the output of this system. Accordingly, the system of the present invention has a much lower noise level and has a more sensitive detection limit. The chart speed=1 cm/min and the detector uses a 20 microliter flow cell with a 20 microliter injection. The lock-in amplifier output is charted as 162 and the corresponding laser amplitude is plotted as 160.

In practice, the optical activity detector is often used with a mass detector (e.g. absorbance detector). When both the mass and net optical rotation are known, the enantiomeric ratio can be calculated. As stated above, imprecise ratios can have disastrous effects in drug and pharmaceutical applications.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown in the drawings and described in the specification.

What is claimed is:

1. An improved optical rotation detector with components fixedly mounted and aligned on an operational bench, said components comprised of:

(I) a laser diode based light source system with a means selected from the group consisting of a fiber optic cable, a cylindrical focusing lens or multiple lenses and prisms for producing a near-gaussian laser beam;

(ii) a first glan-Thompson polarizing prism to improve the linear polarization ratio of said laser beam to at least 1000:1;

(iii) a Faraday rotator utilizing a Terbium Gallium Garnet rod for affecting the polarization of said beam, said rotator being driven by an alternating current source, or reference oscillator, at frequency f;

(iv) a flow cell for directing a solvent and sample flow through said linearly polarized beam, said flow cell having a flow cell body with a central cavity;

a pair of sealing washers selected from the group consisting of chlorotrifluoroethylene, fluorinated ethylene propylene and tetrafluoroethylene a pair of synthetic fused silica hermetically sealed optical windows;

a pair of endcap means for containing said sealing and optical windows, each endcap means having mounting and alignment holes and an attachment means for sealably attaching each said endcap means to each flow cell body end, wherein said endcap and attachment means provides an improved flow cell for passing said laser beam through an optically active substance with minimal mechanical birefringence;

(v) a second glan-Thompson polarizing prism which is oriented 90 degrees from said first polarizing means in its ability to transmit polarized light, wherein said second polarizing means attenuates transmission of most of the polarized laser beam;

(vi) a photodetector for detecting a signal consisting of amplitude modulated light which is transmitted through said second polarizing means;

(vii) a compensator circuitry means for producing a compensated signal which attenuates contributions from frequencies other than f; and (viii) a phase sensitive detector, or lock-in amplifier, as driven by said f frequency oscillator, for sensing the amplitude modulation of the compensated signal at frequency f.

2. The improved optical rotation detector of claim 1, wherein said compensator circuitry means is used to filter out interference and noise contributions from frequencies other than f, said circuitry including low pass and notch filters for filtering said photodetector signal.

3. The improved optical rotation detector of claim 1, wherein said means for producing a near-gaussian laser beam is a length of optical fiber cable.

4. The improved optical rotation detector of claim 1, wherein said means for producing a near-gaussian laser beam includes a cylindrical focusing lens mounted underneath the hermetically sealed optical window containing endcap and on the emitting aperture of the laser diode.

5. The improved optical rotation detector of claim 1, wherein said endcaps include a centralized donut shaped island with a surrounding moat wherein said optical windows are clamped to said endcaps and attached via glue being injected into said moat, wherein said clamps are removed after said glue hardens.

6. The improved optical rotation detector of claim 1, wherein said precision mounting fixture for said flow cell includes a "V" block mount for interfacably cradling said cylindrical flow cell and a top clamping bar which holds said flow cell in place and attaches to said mount, with said interface between said "V" block and said flow cell being machined so that a flow cell can be removed and replaced without further alignment of said detector components.

7. The improved optical rotation detector of claim 1, wherein said components are so ruggedly mounted and prealigned as to provide a system which can be operational for detecing samples within approximately 30–45 minutes for deployment.

8. The optical rotation detector of claim 1, wherein said pair of endcap means is formed from polyetheretherketone.

9. An improved optical rotation detector with components fixedly mounted and aligned on an operational bench, said components comprised of:

(I) a laser light source system with a means for producing a near-gaussian laser beam;

(ii) a first polarizing means to improve the linear polarization ratio of said laser beam to at least 1000:1;

(iii) a Faraday rotator for affecting the polarization of said beam, said rotator being driven by an alternating current source, or reference oscillator, at frequency f;

(iv) a flow cell having a pair of hermetically sealed optical windows, said flow cell for directing a solvent and sample flow through said linearly polarized beam;

(v) a second polarizing means which is oriented 90 degrees from said first polarizing means in its ability to transmit polarized light, wherein said second polarizing means attenuates transmission of most of the polarized laser beam;

(vi) a first photodetector for detecting a signal consisting of amplitude modulated light which is transmitted through said second polarizing means, (vii) a compensator circuitry means for producing a compensated signal which attenuates contributions from frequencies other than f; and (viii) a phase sensitive detector, or lock-in amplifier, as driven by said f frequency oscillator, for sensing the amplitude modulation of the compensated signal at frequency f;

(ix) a second photodetector positioned to detect light reflected from the entrance of said second polarizing means, and said compensator circuitry means is used to subtract out amplitude fluctuations from the laser light source and filter out interference and noise contributions from frequencies other than f, said circuitry including:

(I) at least one low pass filter for filtering said first and second photodetector signals;

(ii) a summing device for operationally subtracting said first and second photodetector signals; and (iii) at least one notch filter for filtering unwanted signal components from the result.

10. The improved optical rotation detector of claim 9, wherein said compensator circuitry means is comprised of operational amplifiers configured to filter and process said photodetector signals.

11. The improved optical rotation detector of claim 10, wherein said compensator circuitry further includes at least one variable resistive device connected to allow controlled balancing of said subtraction operation of said first and second photodetector signals.

12. An improved optical rotation detector comprised of:

a laser diode light source system;

a first polarizing means to improve the linear polarization ratio of said laser beam;

a Faraday rotator;

a flow cell;

a second polarizing means which is oriented 90 degrees from said first polarizing means in its ability to transmit polarized light, wherein said second polarizing means attenuates transmission of most of the polarized laser beam;

a photodetector for detecting a signal consisting of amplitude modulated light which is transmitted through said second polarizing means;

a phase sensitive detector, or lock-in amplifier, as driven by said f frequency oscillator, for sensing the f frequency signal;

the improvement comprising:

(i) a means attached to said laser diode for producing a near-gaussian laser beam;

(ii) a cylindrically shaped flow cell means constructed to minimize mechanical birefringence and dispersion of transmitted light;

(iii) a machined "V"-block mount for precision alignment of said cylindrically shaped flow cell;

(iv) a second photodetector positioned to detect a signal consisting of laser light reflected from the entrance of said second polarizing means;

(v) compensator circuitry means for producing a compensated signal with attenuation of the interference and noise contributions from frequencies other than f.

13. The improved optical rotation detector of claim 12, wherein said compensator circuitry means consists of (i) at least one low pass filter for filtering said first and second photodetector signals;

(ii) a summing device for operationally subtracting said first and second photodetector signals; and (iii) at least one notch filter for filtering unwanted signal components from the summed result.

14. An improved optical rotation detector with components fixedly mounted and aligned on an operational bench, said components comprised of:

(I) a laser diode based light source system with a means selected from the group consisting of a fiber optic cable, a cylindrical focusing lens or multiple lenses and prisms for producing a near-gaussian laser beam;

(ii) a first glan-Thompson polarizing prism to improve the linear polarization ratio of said laser beam to at least 1000:1;

(iii) a Faraday rotator utilizing a Terbium Gallium Garnet rod for affecting the polarization of said beam, said rotator being driven by an alternating current source, or reference oscillator, at frequency f;

(iv) a replaceable, cylindrically shaped flow cell means mounted on a precisioned mounting fixture, said flow cell being used for directing a solvent and sample flow through said linearly polarized beam, said flow cell means utilizing a fused quartz tube through its longitudinal center, said tube having a capillary as the main bore with said capillary being sized sufficiently larger than said beam so as to minimize scattering and subsequent depolarization of said beam;

(v) a second glan-Thompson polarizing prism which is oriented 90 degrees from said first polarizing means in its ability to transmit polarized light, wherein said second polarizing means attenuates transmission of most of the polarized laser beam;

(vi) a detector means for detecting said transmitted light; and;

(v) compensator means for processing said detected signals.

15. The improved optical rotation detector of claim 14, wherein said detector means includes a photodetector and said compensator means includes circuitry for filtering unwanted components from said detected signal.

16. The improved optical rotation detector of claim 15, wherein said detector means includes a first and second photodetector, said compensator means including circuitry for filtering off unwanted components from said detected signals, and circuitry for subtracting said photodetector first signal from said second signal.

* * * * *